US012558172B2

(12) United States Patent  
Huang et al.

(10) Patent No.: US 12,558,172 B2  
(45) Date of Patent: Feb. 24, 2026

(54) SURGICAL ROBOTIC ARM AND SURGICAL ROBOT

(71) Applicant: NOAHTRON INTELLIGENCE MEDTECH (HANGZHOU) CO., LTD., Zhejiang (CN)

(72) Inventors: Shandeng Huang, Zhejiang (CN); Jianfei Liu, Zhejiang (CN); Long Bai, Zhejiang (CN); Xiaohong Chen, Zhejiang (CN)

(73) Assignee: NOAHTRON INTELLIGENCE MEDTECH (HANGZHOU) CO., LTD., Hangzhou (CN)

( * ) Notice: Subject to any disclaimer, the term of this patent is extended or adjusted under 35 U.S.C. 154(b) by 721 days.

(21) Appl. No.: 17/794,951

(22) PCT Filed: Jul. 15, 2020

(86) PCT No.: PCT/CN2020/101998
§ 371 (c)(1),
(2) Date: Jul. 22, 2022

(87) PCT Pub. No.: WO2021/147267
PCT Pub. Date: Jul. 29, 2021

(65) Prior Publication Data
US 2023/0079591 A1　Mar. 16, 2023

(30) Foreign Application Priority Data

Jan. 23, 2020　(CN) ......................... 202010076420.3
Jan. 23, 2020　(CN) ......................... 202020149829.9

(51) Int. Cl.
*A61B 34/30* (2016.01)
*A61B 17/00* (2006.01)
(Continued)

(52) U.S. Cl.
CPC .............. *A61B 34/30* (2016.02); *B25J 9/0066* (2013.01); *A61B 2017/00323* (2013.01);
(Continued)

(58) Field of Classification Search
CPC ........... A61B 2017/00323; A61B 2017/00991; A61B 34/30; A61B 2034/301;
(Continued)

(56) References Cited

U.S. PATENT DOCUMENTS

| 4,819,496 | A | * | 4/1989 | Shelef | .................. B25J 17/0216 |
| | | | | | 901/29 |
| 5,053,687 | A | * | 10/1991 | Merlet | ................. B25J 17/0216 |
| | | | | | 318/566 |

(Continued)

FOREIGN PATENT DOCUMENTS

| CA | 3035284 A1 | * | 3/2018 | ............. A61B 17/00 |
| CN | 101400476 A | * | 4/2009 | ........... B23Q 1/5462 |

(Continued)

OTHER PUBLICATIONS

Serdar Kucuk et al., "Inverse Kinematics Solution of a New Hybrid Robot Manipulator Proposed for Medical Purposes", 2016 IEEE, 978-1-5090-2386-8/16.

(Continued)

*Primary Examiner* — Kevin T Truong
(74) *Attorney, Agent, or Firm* — Bridgeway IP Law Group, PLLC; Sang Ho Lee; Hyun Woo Shin

(57) ABSTRACT

A surgical robotic arm includes a presurgical positioning assembly, a telecentric manipulating assembly and an executing assembly; the telecentric manipulating assembly includes a static platform, a first movable platform and a plurality of first telescopic elements disposed between the static platform and the first movable platform; the executing assembly has a preset telecentric fixed point; the plurality of (Continued)

first telescopic elements are capable of moving the first movable platform; a swing center of the executing assembly is the telecentric fixed point.

25 Claims, 5 Drawing Sheets

(51) Int. Cl.
| | |
|---|---|
| *B25J 9/00* | (2006.01) |
| *A61B 90/00* | (2016.01) |

(52) U.S. Cl.
CPC ............... *A61B 2017/00991* (2013.01); *A61B 2034/301* (2016.02); *A61B 2034/304* (2016.02); *A61B 2090/066* (2016.02)

(58) Field of Classification Search
CPC ........ A61B 2034/302; A61B 2034/304; A61B 2090/064; A61B 2090/066; B25J 17/0216; B25J 17/0275; B25J 9/0063; B25J 9/0066; B25J 9/0096; B25J 9/003
See application file for complete search history.

(56) References Cited

U.S. PATENT DOCUMENTS

| | | | |
|---|---|---|---|
| 5,279,309 A | | 1/1994 | Taylor et al. |
| 5,651,574 A | * | 7/1997 | Tanikawa ................... B25J 9/12 |
| | | | 901/29 |
| 5,987,726 A | * | 11/1999 | Akeel ................. B25J 17/0216 |
| | | | 29/709 |
| 6,477,912 B2 | * | 11/2002 | Song ....................... F16H 21/46 |
| | | | 901/29 |
| 12,089,910 B2 | | 9/2024 | Zhang et al. |
| 2003/0106230 A1 | * | 6/2003 | Hennessey ........... B25J 17/0216 |
| | | | 33/645 |
| 2010/0122602 A1 | * | 5/2010 | Marcroft ............. B25J 17/0216 |
| | | | 901/18 |
| 2011/0282358 A1 | | 11/2011 | Gomez et al. |
| 2014/0194699 A1 | | 7/2014 | Roh et al. |
| 2015/0005785 A1 | * | 1/2015 | Olson .................... G16H 40/67 |
| | | | 901/9 |
| 2016/0249990 A1 | | 9/2016 | Glozman et al. |
| 2016/0346050 A1 | | 12/2016 | Schena et al. |
| 2016/0361128 A1 | | 12/2016 | Seeber |
| 2017/0112579 A1 | * | 4/2017 | Yen ...................... B25J 15/0019 |
| 2018/0000548 A1 | * | 1/2018 | Olds ....................... A61B 34/35 |
| 2018/0214167 A1 | | 8/2018 | Overmyer et al. |
| 2018/0333207 A1 | | 11/2018 | Moctezuma De La Barrera |
| 2019/0380795 A1 | | 12/2019 | Tsao et al. |
| 2020/0009001 A1 | * | 1/2020 | Xue ...................... B25J 9/0066 |
| 2021/0192759 A1 | | 6/2021 | Lang |
| 2022/0280193 A1 | | 9/2022 | Tal |
| 2022/0409282 A1 | | 12/2022 | Shochat et al. |
| 2023/0255701 A1 | | 8/2023 | Post et al. |

FOREIGN PATENT DOCUMENTS

| | | | | |
|---|---|---|---|---|
| CN | 101919739 A | * | 12/2010 | |
| CN | 102892375 A | | 1/2013 | |
| CN | 104546147 A | | 4/2015 | |
| CN | 104739487 A | | 7/2015 | |
| CN | 105965557 A | * | 9/2016 | ............ B26B 19/02 |
| CN | 106725855 A | | 5/2017 | |
| CN | 107037823 A | * | 8/2017 | .......... G05D 1/0891 |
| CN | 107775627 A | * | 3/2018 | |
| CN | 108210070 A | | 6/2018 | |
| CN | 108433814 A | | 8/2018 | |
| CN | 108524000 A | | 9/2018 | |
| CN | 108697481 A | | 10/2018 | |
| CN | 109199591 A | * | 1/2019 | |
| CN | 109316241 A | * | 2/2019 | ............ A61B 34/20 |
| CN | 208598522 U | | 3/2019 | |
| CN | 110279469 A | | 9/2019 | |
| CN | 111134847 A | | 5/2020 | |
| CN | 111214291 A | | 6/2020 | |
| CN | 111227940 A | | 6/2020 | |
| CN | 111227943 A | | 6/2020 | |
| CN | 111227944 A | | 6/2020 | |
| CN | 111249008 A | | 6/2020 | |
| CN | 111329581 A | | 6/2020 | |
| EP | 3305474 A1 | | 5/2016 | |
| ES | 2390436 A1 | | 11/2012 | |
| JP | 2017104450 A | * | 6/2017 | ............ A61B 34/30 |
| WO | WO-2011143024 A1 | * | 11/2011 | ......... A61B 1/00135 |
| WO | 2013/067535 A1 | | 5/2013 | |
| WO | WO-2015168799 A1 | * | 11/2015 | .......... B25J 17/0216 |

OTHER PUBLICATIONS

Irena Tsui et al., "Robotic Surgery in Ophthalmology", Robot Surgery, Jan. 1, 2010, pp. 149-164, ISBN 978-953-7619-77-0, Intech, Croatia.

Zhang Zhenchuan et al., "Design and Kinematic Analysis of a Parallel Robot with Remote Center of Motion for Minimally Invasive Surgery", 2015 IEEE, International Conference on Mechatronics and Automation, Aug. 2, 2015, pp. 698-703, ISBN 978-1-4799-7098-8/15, Beijing, China.

Gallardo-Alvarado, Jaime et al., "Kinematics and dynamics of 2(3-RPS) manipulators by means of screw theory and the principle of virtual work", Mechanism and Machine Theory, vol. 43, No. 10 (2008), pp. 1281-1294, Oct. 1, 2008.

\* cited by examiner

SURGICAL ROBOTIC ARM AND SURGICAL ROBOT

RELEVANT APPLICATION

The present application claims the priority of Chinese patent application with the application date of Jan. 23, 2020, the application number of 202020149829.9 and the title of the invention "SURGICAL ROBOTIC ARM AND SURGICAL ROBOT"; and Chinese patent application with the application date of Jan. 23, 2020, the application number of 202010076420.3 and the title of the invention "SURGICAL ROBOTIC ARM AND SURGICAL ROBOT", of which all the contents are incorporated into the present application by reference.

TECHNICAL FIELD

The present disclosure relates to the technical field of medical devices, in particular to a surgical robotic arm and a surgical robot.

BACKGROUND

The birth of minimally invasive surgery largely overcomes the defects of traditional surgery, such as large knife edge, large amount of bleeding, many complications, high surgery risk and others. Because of the rapid development in recent years, minimally invasive surgery is gradually gaining the favor of medical staff and patients, and has become a new field of medical research and clinical application.

Assisting doctors with minimally invasive surgery using surgical robots can make the surgical operation more sensitive and accurate. Taking Da Vinci surgical robot as an example, the Da Vinci surgical robot can amplify the doctor's field of vision ten times, effectively filter out the doctor's hand trembling at the same time, and has a wide clinical application in the field of minimally invasive surgery.

The surgical robotic arm applicable to the surgical robot needs to drive the surgical instrument to perform the surgical operation, and the surgical instrument needs to realizing reaching into the patient's body by extending into a tiny wound opened on the skin surface. This requires the surgical instrument to perform the surgical operation in a stable and non-trembling state with the tiny wound opened on the skin surface as a telecentric fixed point. However, the current surgical robotic arm applicable to the surgical robot cannot fully meet the requirements in clinical performance. The current surgical robotic arm is relatively weak in the load capacity and execution accuracy of the surgical instrument. The weakness of the surgical robotic arm in the load capacity and execution accuracy limits the clinical application of the surgical robot.

SUMMARY

According to various embodiments of the present disclosure, a surgical robotic arm is provided, including a presurgical positioning assembly, a telecentric manipulating assembly and an executing assembly, the telecentric manipulating assembly includes a static platform, a first movable platform and a plurality of first telescopic elements disposed between the static platform and the first movable platform, a side of the static platform relatively far away from the first movable platform is fixedly connected to the presurgical positioning assembly, a side of the first movable platform relatively far away from the static platform is fixedly connected to the executing assembly, and both ends of each first telescopic element are rotationally connected to the static platform and the first movable platform respectively;

the executing assembly has a preset telecentric fixed point; coordinated extension and retraction of the plurality of first telescopic elements can control the first movable platform to move relative to the static platform and drive the executing assembly to extend and retract and swing; a swing center of the executing assembly is the telecentric fixed point; and a telescopic path of the executing assembly passes through the telecentric fixed point.

The present disclosure further provides a surgical robot, including a surgical robotic arm, and the surgical robotic arm is the surgical robotic arm according to various embodiments of the present disclosure.

DESCRIPTION OF DRAWINGS

In order to better describe and explain embodiments and/or examples of those disclosed herein, one or more drawings may be referred to. Additional details or examples for describing the drawings should not be considered as the limiting of the scope of any of the disclosed, currently described embodiments and/or examples and the best modes of these as currently understood.

DETAILED DESCRIPTION OF THE EMBODIMENTS

The technical solutions in the embodiments of the present disclosure will be clearly and completely described below in conjunction with the drawings in the embodiments of the present disclosure, and obviously, the described embodiments are only some embodiments of the present disclosure, rather than the entire embodiments. Based on the embodiments of the present disclosure, all the other embodiments obtained by those ordinary technical persons in the art belong to scopes protected by the present disclosure without the premise of creative efforts.

It should be noted that when an assembly is called "installed on" another assembly, it can be directly installed on another assembly or there may also be intermediate assemblies. When an assembly is considered to be "disposed on" another assembly, it can be directly disposed on another assembly or there may be intermediate assemblies at the same time. When an assembly is considered to be "fixed on" another assembly, it can be directly fixed on another assembly or there may be intermediate assemblies at the same time.

Unless otherwise defined, all technical and scientific terms used herein have the same meanings as those commonly understood by those skilled in the technical field of the present disclosure. The terms used in the description of the present disclosure herein are only for the purpose of describing specific embodiments, and are not intended to limit the present disclosure. The term "or/and" used herein includes any and all combinations of one or more relevant listed items.

Figure 1:
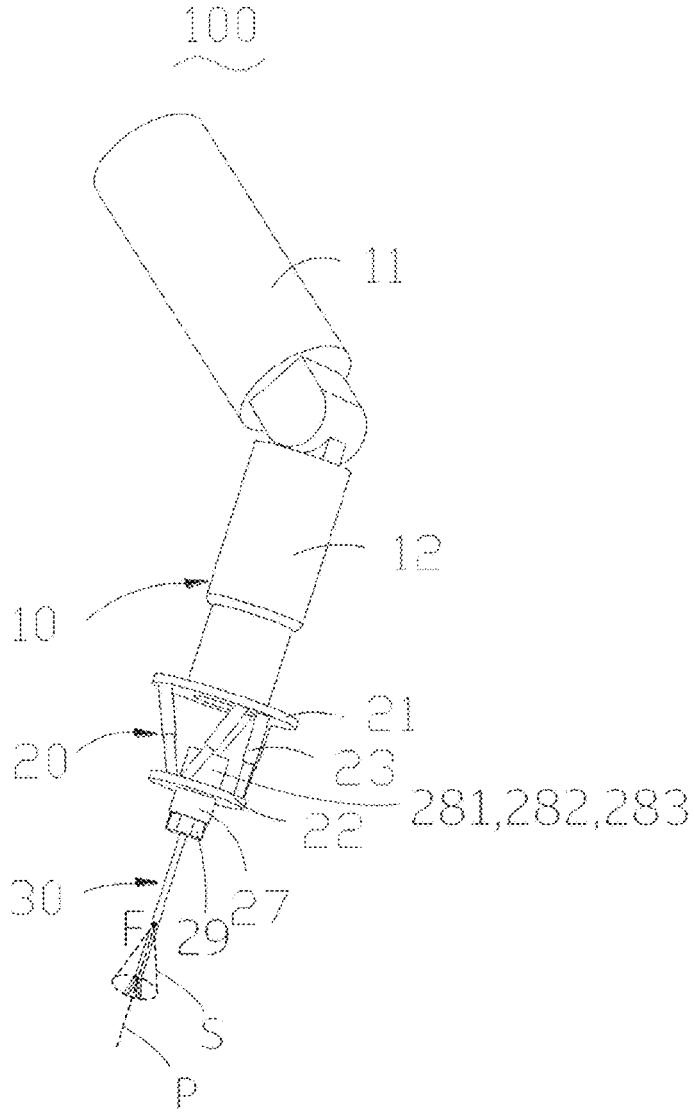
FIG. 1 is a structural diagram of a surgical robotic arm in a first embodiment of the present disclosure.
Figure 2:
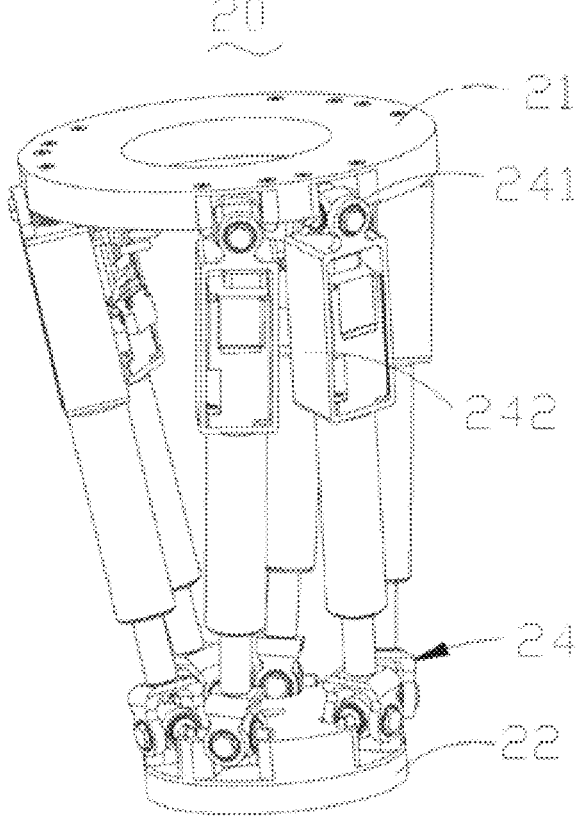
FIG. 2 is a structural diagram of a telecentric manipulating assembly shown in FIG. 1.

Please refer to FIG. 1 and FIG. 2, FIG. 1 is a structural diagram of a surgical robotic arm 100 in a first embodiment of the present disclosure; and FIG. 2 is a structural diagram of a telecentric manipulating assembly 20 shown in FIG. 1.

The present disclosure provides a surgical robotic arm 100 which is used in Da Vinci surgical robot. In the present embodiment, the surgical robotic arm 100 is used to assist doctors to perform complex surgeries through a minimally invasive method. It may be understood that in other embodiments, the surgical robotic arm 100 may also be applied to other medical devices to assist doctors to perform surgeries.

The Da Vinci surgical robot usually includes a console, an image processing apparatus and a surgical robotic arm 100, the console is used for a chief surgeon to perform analog control operations, and the console is coupled with the surgical robotic arm 100 and may transfer the analog control operations to the surgical robotic arm 100; the image processing apparatus may present the image viewed by the endoscope in real time, and may also enlarge the image viewed by the endoscope, thereby making the doctor's surgical field of vision clearer; and the surgical robotic arm 100 is used for minimally invasive surgery on patients, and the motion track and surgical process of the surgical robotic arm 100 may be transferred to the image processing apparatus through the endoscope.

The console usually includes a main controller and a foot pedal controller, the main controller is coupled to the surgical robotic arm 100 and moves synchronously with the surgical robotic arm 100, the doctor controls the surgical robotic arm 100 for positioning through the main controller, and opens and closes the working state of the surgical robotic arm 100 through the foot pedal controller. The main controller not only may filter the micro trembling of the doctor's hand, but also may reduce the moving distance of the doctor's hand proportionally, and cooperates with the enlarged endoscope image in the image processing apparatus, the doctor's eye and hand coordination may be greatly improved, thereby ensuring the surgical accuracy.

The image processing apparatus is coupled to the endoscope, which may present the image viewed by the endoscope in real time, and may enlarge the image viewed by the endoscope when necessary, and the magnification may be adjusted according to different surgical needs. It may be understood that after the magnification of the endoscope is adjusted, the doctor may synchronously adjust the magnification of the movement distance of the doctor's hand in the main controller at the time of proportional reduction, so that the magnification of the endoscope is appropriate to the magnification of the main controller at the time of proportional reduction, thereby ensuring the doctor's eye and hand coordination to the greatest extent and improving the surgical accuracy.

The endoscope at least has a lighting function and an image acquisition function. The endoscope has a three-dimensional lens, which is basically consistent with the image when people directly look at it. The image captured by the endoscope has high resolution and may be used for subsequent amplification processing by the image processing apparatus.

The surgical robotic arm 100 provided by the present disclosure includes a presurgical positioning assembly 10, a telecentric manipulating assembly 20 and an executing assembly 30, and the presurgical positioning assembly 10, the telecentric manipulating assembly 20 and the executing assembly 30 are connected in sequence. The presurgical positioning assembly 10 is used to roughly move the executing assembly 30 to a position close to a lesion; the telecentric manipulating assembly 20 is used to control the executing assembly 30 to move within a small range; and the executing assembly 30 is used to perform surgical operations.

Specifically, the presurgical positioning assembly 10 may drive the executing assembly 30 to perform a large-scale position adjustment. The presurgical positioning assembly 10 includes at least one of at least one moving arm 11 or at least one telescopic arm 12, the moving arm 11 has two degrees of freedom and may drive the executing assembly 30 to translate and rotate; and the telescopic arm 12 has a degree of freedom and may drive the executing assembly 30 to translate.

The telecentric manipulating assembly 20 may drive the executing assembly 30 to make fine position adjustment with the telecentric fixed point as a swing center (for example the point F as shown in FIG. 1). Generally, the telecentric manipulating assembly 20 has multiple degrees of freedom at the same time and may drive the executing assembly 30 to perform flexible surgical operations.

The executing assembly 30 includes a surgical instrument 32, and the surgical instrument 32 is located at an end portion of the executing assembly 30 and the surgical instrument 32 may perform micro movement through its own swing, rotation and other actions to perform surgical operations. The surgical instrument 32 may be an electric scalpel, forceps, clip or hook, or other surgical instruments, which will not be described here. The surgical instrument 32 is usually detachably installed at the end portion of the executing assembly 30, and according to different surgical needs or according to the needs of different surgical stages of the same operation, different surgical instruments 32 may be changed to complete different surgical operations.

At present, the surgical robotic arm of Da Vinci surgical robot for performing surgical actions adopts a serial mechanism. In order to meet the requirements of the end motion accuracy, load and telecentric fixed point, the requirement for manufacturing process of the surgical robotic arm, including materials, processing accuracy and the like, is very high, resulting in extremely high manufacturing cost; and the characteristics of the serial mechanism make the structure of the robotic arm slender, and the interference and collision of multiple robotic arms sometimes occur during the operation, which will affect the normal operation. In addition, there are strict requirements for the material structure and control mode of the surgical instrument installed at its end. For example, the rotation, swing, clamping and other actions of the surgical instrument are driven by the steel cable, the rotation of the instrument will make the swing, clamping and other actions to drive the steel cable to be distorted and deformed, the service life of the surgical instrument is strictly limited and the use cost is high; furthermore, the accurate detection of the end force of the instrument is affected, and it is difficult to realize the feedback function of contact force.

In the surgical robotic arm 100 provided by the present disclosure, the telecentric manipulating assembly 20 includes a static platform 21, a first movable platform 22 and a plurality of first telescopic elements 23 disposed between the static platform 21 and the first movable platform 22, a side of the static platform 21 relatively far away from the first movable platform 22 is fixedly connected to the presurgical positioning assembly 10, a side of the first movable platform 22 relatively far away from the static platform 21 is fixedly connected to the executing assembly 30, and both ends of each first telescopic element 23 are rotationally connected to the static platform 21 and the first movable platform 22 respectively; the executing assembly 30 has a preset telecentric fixed point (for example the point F as shown in FIG. 1); coordinated extension and retraction among the plurality of first telescopic elements 23 may control the first movable platform 22 to move relative to the static platform 21 and drive the executing assembly 30 to extend and retract and swing; a swing center of the executing assembly 30 is the telecentric fixed point; and a telescopic path (for example the path P as shown in FIG. 1) of the executing assembly 30 passes through the telecentric fixed point.

With this disposition, the presurgical positioning assembly 10 only needs to roughly move the executing assembly 30, while the telecentric manipulating assembly 20 realizes the accurate control of the executing assembly 30. Thus, the number of positioning units in the presurgical positioning assembly 10 may be reduced accordingly, thereby reducing the accumulation of multiple positioning unit errors and response time, so as to improve the accuracy of surgery. Secondly, the plurality of the first telescopic elements 23 in the telecentric manipulating assembly 20 are disposed in parallel rather than in series, and errors of the plurality of the first telescopic elements 23 may not be transferred cumulatively, but may offset each other. In addition, since each of the first telescopic elements 23 is driven independently, the response time of the plurality of first telescopic elements 23 will not be transferred cumulatively. Thus, the accurate control of the executing assembly 30 realized by the telecentric manipulating assembly 20 may reduce the displacement error in the surgery and shorten the response time. On the other hand, since the telecentric manipulating assembly 20 improves the control accuracy of the executing assembly 30, the executing assembly 30 may carry a larger load under the condition of the same accuracy as the traditional Da Vinci surgical robot, more complex surgery may be completed. In addition, the executing assembly 30 may swing with the telecentric fixed point as the swing center during the surgical operation, therefore, it is only necessary to open a tiny wound on the patient's skin surface for the executing assembly 30 to pass through, the wound of the patient is small and the postsurgical recovery is fast.

Specifically, the first telescopic element 23 is optionally an electric cylinder. As an optional choice, in order to make the surgical robotic arm 100 develop to miniaturization, the electric cylinder is a small electric cylinder, as long as it can drive the load motion in the surgery.

It should be particularly noted that the telecentric fixed point referred to herein refers to a fixed point selected and fixed along the length direction of the executing assembly 30, and under the control action of the telecentric manipulating assembly 20, the movement performed by the executing assembly 30 has the regularity of swinging around the point, and the point does not displace. Specifically, the swing of the surgical instrument 32 may take the telecentric fixed point as the swing center, and the front and back telescopic movement of the executing rod 31 may move along the telecentric fixed point.

In the specific surgery process, the position of the telecentric fixed point is the position of the wound on the human skin surface during the surgery; the movement of the executing assembly 30 has the purpose of regularity relative to the telecentric fixed point, so as to ensure that the area of the human wound may not be expanded due to the movement of the instrument during the movement of the executing assembly 30, which is the premise of minimally invasive surgery.

It should be additionally emphasized that the position of the telecentric fixed point is not necessarily fixed during the whole operation, and the position of the telecentric fixed point is selected in a single surgical operation and may be changed in different surgical operations. For example, doctors perform surgical operations at different wounds, the surgical operations performed at these two wounds may enable the control apparatus to select telecentric fixed points at different positions in different time periods according to the actual parameters such as the length of the executing rod 31, as long as the movement under a single surgical operation can form a regular movement relative to the telecentric fixed point. In order to improve the flexibility of the surgical robotic arm 100, in one embodiment of the present disclosure, a swing limit angle of the executing assembly 30 relative to the telecentric fixed point is disposed as ±20°, and the executing assembly 30 may swing in a conical space (for example the space S as shown in FIG. 1) with a telescopic path of the executing assembly 30 as an axis and a vertex angle of 40°.

With this disposition, the executing assembly 30 is relatively flexible, may move in a relatively large range, and may assist doctors to realize more complex surgical operations.

In order to improve the stability of the surgical robotic arm 100, in one embodiment of the present disclosure, a plurality of rotation connecting points 24 between the first telescopic element 23 and the first movable platform 22 are disposed in a circle, and the rotation connecting points 24 between the first telescopic element 23 and the static platform 21 are disposed in a circle; and a circular diameter enclosed and formed by the rotation connecting points 24 on the static platform 21 is 1 to 2 times the circular diameter enclosed and formed by the rotation connecting points 24 on the first movable platform 22.

With this disposition, the first movable platform 22 has fewer tremors in the process of moving relative to the static platform 21, and a total error between the respective first telescopic elements 23 may compensate for each other, so as to improve the stability of the surgical robotic arm 100.

It may be understood that the sections of the static platform 21 and the first movable platform 22 in the radial direction may be circular, polygonal, or in other irregular shapes, as long as the plurality of rotation connecting points 24 of each first telescopic element 23 are disposed in a circle on the static platform 21 and the first movable platform 22.

In order to further improve the stability of the surgical robotic arm 100, in one embodiment of the present disclosure, the circular diameter enclosed and formed by the rotation connecting points 24 located on the static platform 21 is 1.7 times the circular diameter enclosed and formed by the rotation connecting points 24 located on the first movable platform 22.

With this disposition, the first movable platform 22 has a minimum tremor in the process of moving relative to the static platform 21, furthermore, a space volume occupied by the first movable platform 22 and the static platform 21 may be relatively compressed, and there is the most balanced combination between structure lightweight and high performance.

In order to realize the rotating connection between the first telescopic element 23 and the first movable platform 22 and the static platform 21, in one embodiment of the present disclosure, both ends of the first telescopic element 23 are respectively provided with a ball hinge joint and a Hooke hinge joint 241; the first telescopic element 23 is connected to one of the static platform 21 and the first movable platform 22 through the ball hinge joint, and is connected to the other of the static platform 21 and the first movable platform 22 through the Hooke hinge joint 241.

With this disposition, both ends of the first telescopic element 23 may be rotationally connected with the first movable platform 22 and the static platform 21, respectively, and the connection performance of the first telescopic element 23 is better. The actuation principle thereof is: the ball joint has three degrees of freedom, and the Hooke hinge joint 241 has two degrees of freedom, the ball joint and the Hooke hinge joint 241 are respectively disposed at both ends of the first telescopic element 23, so that the first movable platform 22 may realize the movement of six degrees of freedom.

In order to take into account the cost on the basis of realizing the rotating connection between the first telescopic element 23 and the first movable platform 22 and the static platform 21, in one embodiment of the present disclosure, the surgical robotic arm 100 further includes a cylinder sleeve 242, and the cylinder sleeve 242 is sleeved and rotationally connected to the first telescopic element 23; Hooke hinge joints 241 are respectively disposed on one end of the cylinder sleeve 242 relatively far away from the first telescopic element 23 and on one end of the first telescopic element 23 relatively far away from the cylinder sleeve 242; one of the cylinder sleeve 242 and the first telescopic element 23 is connected to the first movable platform 22 through the corresponding Hooke hinge joint 241; and the other of the cylinder sleeve 242 and the first telescopic element 23 is connected to the static platform 21 through the corresponding Hooke hinge joint 241.

With this disposition, the first telescopic element 23 may realize the power transmission between the first movable platform 22 and the static platform 21 through the Hooke hinge joint 241 with low manufacturing difficulty and low cost, and it is not necessary to dispose an expensive and easily damaged ball hinge joint, thereby having a better cost performance advantage. The actuation principle thereof is: The Hooke hinge joints 241 at both ends of the first telescopic element 23 have two degrees of freedom, and the cylinder liner 242 has one degree of freedom, which may realize the telescopic movement of the first telescopic element 23 in the axial direction, so that the first movable platform 22 may realize the movement of six degrees of freedom.

It may be understood that in other embodiments, other joints may also be used to realize the connection between the first telescopic element 23 and the first movable platform 22 and the static platform 21, as long as the first movable platform 22 has a certain degree of freedom and can drive the executing assembly 30 to complete the surgical operation.

In order to improve the moving stability of the surgical robotic arm 100, in one embodiment of the present disclosure, the number of the first telescopic elements 23 is six, and the respective rotation connecting points 24 between the first telescopic element 23 and the first movable platform 22 are all disposed spaced apart from each other; and the respective rotation connecting points 24 between the first telescopic element 23 and the static platform 21 are also all disposed spaced apart from each other.

With this disposition, by adopting the distribution form of interval rotation connecting points 24, the tremor interference between the respective first telescopic elements 23 is reduced, and the moving stability of the surgical robotic arm

100 may be further improved. In addition, when the six first telescopic elements 23 drive the first movable platform 22 to move, they can not only realize the multi-directional and comprehensive movement of the first movable platform 22, but also do not cause too redundant kinematic analysis to slow down the calculation speed.

It may be understood that in other embodiments, the number of the first telescopic elements 23 may also be three, four, five or even more, as long as the first movable platform 22 can drive the executing assembly 30 to complete the surgical operation.

Figure 3:
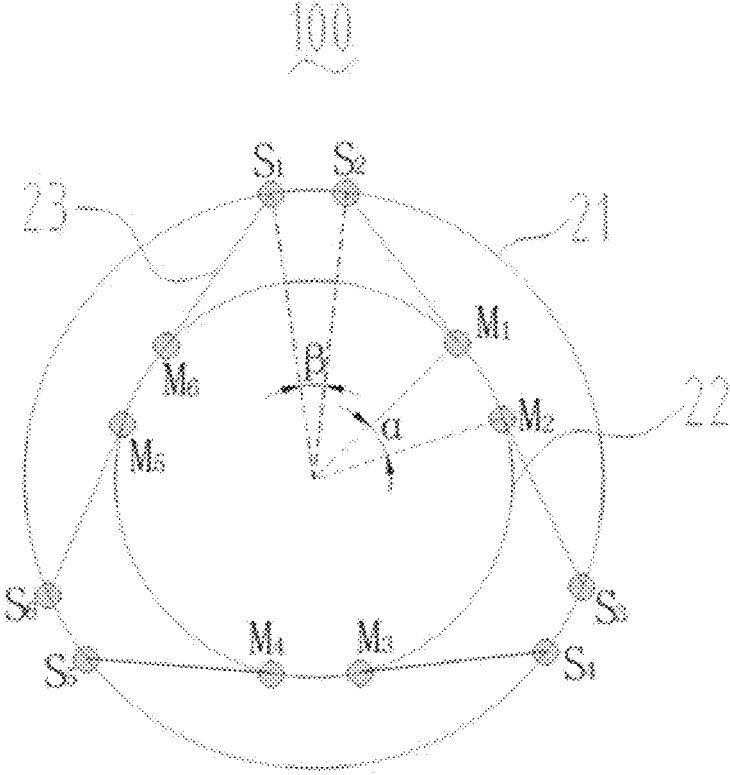
FIG. 3 is a structural diagram of the telecentric manipulating assembly shown in FIG. 2 from a top view.

Please also refer to FIG. 3, FIG. 3 is a structural diagram of the telecentric manipulating assembly 20 shown in FIG. 2 from a top view. In order to further improve the moving stability of the surgical robotic arm 100 and facilitate realizing kinematic analysis, in one embodiment of the present disclosure, the respective rotation connecting points 24 between the first telescopic element 23 and the first movable platform 22 are paired in a nearby way; and a first included angle $\alpha$ is correspondingly formed between each group of the same pair of two rotation connecting points 24 and a center of the first movable platform 22, and a size of each of the first included angles $\alpha$ is equal.

There are six rotation connecting points 24 between the first telescopic element 23 and the first movable platform 22, which are respectively marked as $M_1$ to $M_6$; the six rotation connecting points 24 are paired in a nearby combination way, that is, the two nearest rotation connecting points 24 are paired, thereby forming three pairing relationships of $M_1$ and $M_2$, $M_3$ and $M_4$, $M_5$ and $M_6$. Each pairing relationship, that is, every two rotation connecting points 24 form a first included angle $\alpha$ with the center of the first movable platform 22, and angles of three first included angles $\alpha$ are equal.

In this case, the first telescopic elements 23 will form a symmetrical distribution on the first movable platform 22, which is conducive to improving the moving stability of the surgical robotic arm 100.

Optionally, an angle range of the first included angle $\alpha$ is $15°$ to $60°$. In this case, the included angle range between the respective rotation connecting points 24 between the first telescopic element 23 and the first movable platform 22 is in a better section, which is not only conducive to ensuring the moving stability, but also can facilitate realizing the moving analysis of telescopic amount of each first telescopic element 23 through a relatively appropriate included angle range.

In order to further improve the moving stability of the surgical robotic arm 100, the respective rotation connecting points 24 between the first telescopic element 23 and the static platform 21 are paired in a nearby way; and a second included angle $\beta$ is correspondingly formed between two rotation connecting points 24 of the same pair and a center of the static platform 21, and a size of each second included angle $\beta$ is equal.

There are six rotation connecting points 24 between the first telescopic element 23 and the static platform 21, which are respectively marked as $S_1$ to $S_6$; the six rotation connecting points 24 are paired in a nearby combination way, that is, the two nearest rotation connecting points 24 are paired, thereby forming three pairing relationships of $S_1$ and $S_2$, $S_3$ and $S_4$, $S_5$ and $S_6$. Each pairing relationship, that is, every two rotation connecting points 24 form a second included angle $\beta$ with a center of the static platform 21, and angles of three second included angles $\beta$ are equal.

In this case, the first telescopic elements 23 will form a symmetrical distribution on the static platform 21, which is conducive to improving the moving stability of the surgical robotic arm 100.

Optionally, an angle range of the second included angle β is 60° to 105°.

In this case, the included angle range between the respective rotation connecting points 24 between the first telescopic element 23 and the static platform 21 is in a better section, which is not only conducive to ensuring the moving stability, but also can facilitate realizing the moving analysis of telescopic amount of each first telescopic element 23 through a relatively appropriate included angle range.

Optionally, the pairing manner of the respective rotation connecting points 24 of the first telescopic element 23 on the static platform 21 is staggered from the pairing manner of the respective rotation connecting points 24 of the corresponding first telescopic element 23 on the first movable platform 22, that is, the same pair of rotation connecting points 24 of the first telescopic element 23 on the static platform 21 is not paired with the two rotation connecting points 24 of the corresponding first telescopic element 23 on the first movable platform 22.

In the traditional Da Vinci surgical robot, a driving motor drives the surgical instrument to rotate by driving the transmission cable, but the transmission cables may be mutually winded inside the executing rod during the rotation process, which may affect the surgical accuracy.

In order to avoid the occurrence of winding of transmission cables during the rotation of the surgical instrument 32, in one embodiment of the present disclosure, the executing assembly 30 includes an executing rod 31 and a surgical instrument 32 disposed at one end of the executing rod 31 relatively far away from the first movable platform 22, the first movable platform 22 is provided with a rotation driving part 27, the rotation driving part 27 is connected to the executing rod 31 and may drive the executing rod 31 and the surgical instrument 32 to rotate synchronously along the axial direction of the executing rod 31.

With this disposition, the surgical instrument 32 will rotate synchronously with the executing rod 31, so as to avoid the mutual winding of the transmission cables when rotating relative to the executing rod 31.

Specifically, the rotation driving part 27 is installed on a side of the first movable platform 22 close to the executing assembly 30, and the rotation driving part 27 is directly connected to the executing rod 31 and can drive the executing rod 31 to rotate synchronously with the surgical instrument 32. The rotation driving part 27 is optionally a motor.

In order to make the movement of the surgical instrument 32 more flexible and accurate, in one embodiment of the present disclosure, the first movable platform 22 is also provided with a first deflection driving part 281, a second deflection driving part 282 and an open-close driving part 283, the executing rod 31 is hollow and contains transmission cables, and the surgical instrument 32 is connected to the first deflection driving part 281, the second deflection driving part 282 and the open-close driving part 283 through the transmission cable; and the first deflection driving part and the second deflection driving part can respectively drive the surgical instrument 32 to deflect in two different staggered directions through the transmission cable, and the open-close driving part can drive the surgical instrument 32 to open and close through the transmission cable.

With this disposition, the surgical instrument 32 can be flexibly deflected and opened and closed under the cooperative action of the first deflection driving part, the second deflection driving part and the open-close driving part, and the simultaneous driving of a plurality of driving parts can reduce the displacement error and delay error during driving.

Specifically, the first deflection driving part 281, the second deflection driving part 282 and the open-close driving part 283 are all installed on the first movable platform 22.

Optionally, in order to miniaturize the telecentric manipulating assembly 20, the first deflection driving part 281, the second deflection driving part 282 and the open-close driving part 283 are all installed at a side of the first movable platform 22 far away from the executing assembly 30, and are located in the middle of the first movable platform 22, which will not affect the arrangement of the first telescopic elements 23. It may be understood that in other embodiments, the first deflection driving part, the second deflection driving part and the open-close driving part may also be installed at other positions, as long as the surgical machine can be controlled through the transmission cable.

Specifically, the first deflection driving part, the second deflection driving part and the open-close driving part are optionally three motors.

Figure 4:
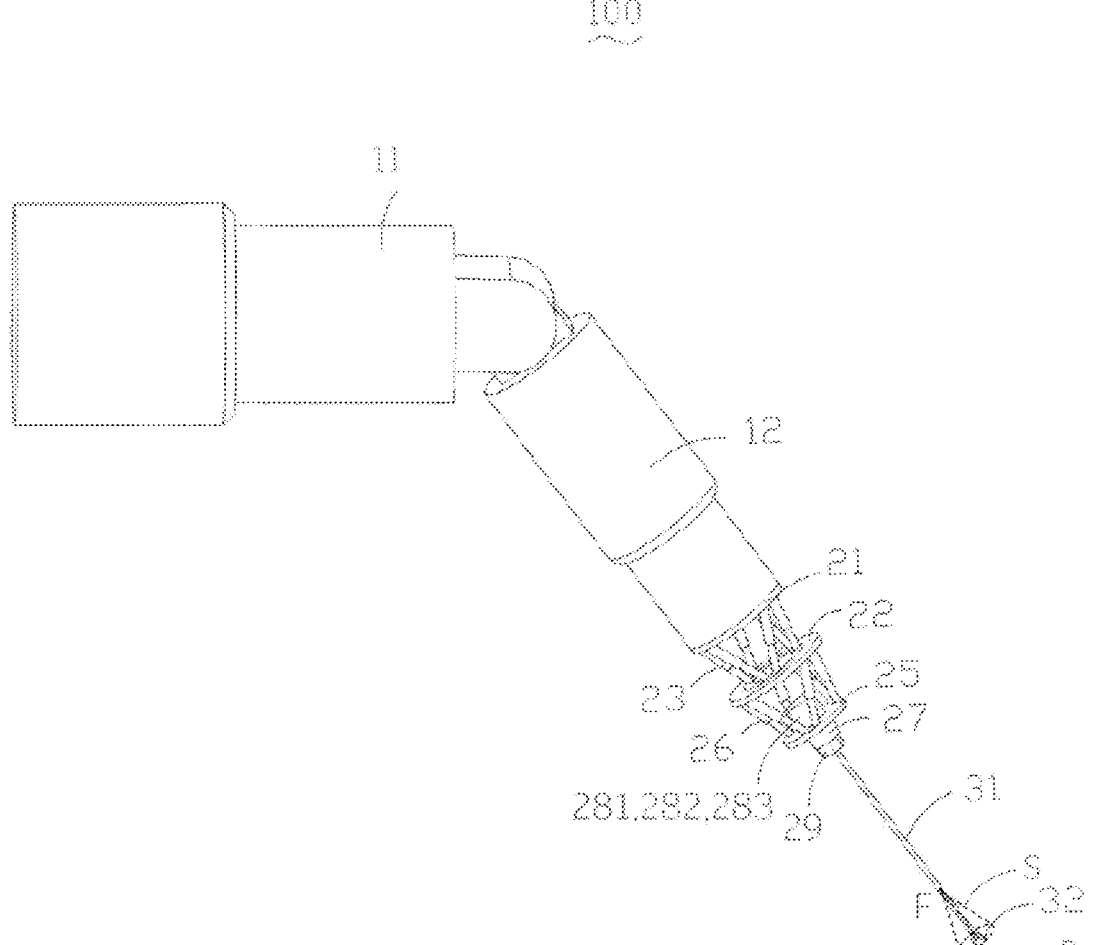
FIG. 4 is a structural diagram of a surgical robotic arm in a second embodiment of the present disclosure.
Figure 5:
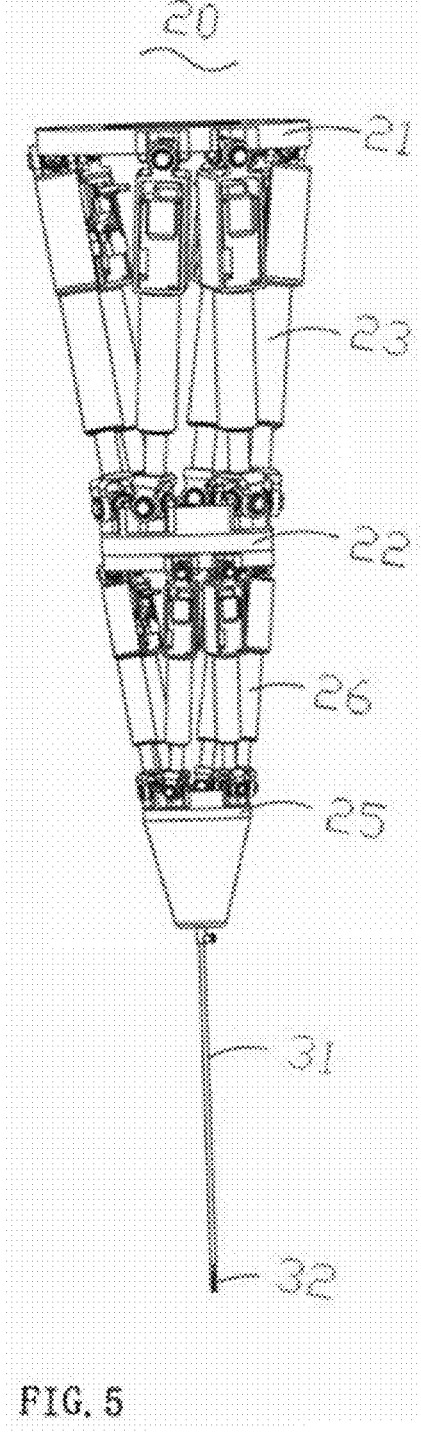
FIG. 5 is a structural diagram of the telecentric manipulating assembly shown in FIG. 4.

Please refer to FIG. 4 and FIG. 5 together, FIG. 4 is a structural diagram of a surgical robotic arm 100 in a second embodiment of the present disclosure; and FIG. 5 is a structural diagram of a telecentric manipulating assembly 20 shown in FIG. 4.

In order to realize more complex surgical contents, in one embodiment of the present disclosure, the telecentric manipulating assembly 20 further includes a second movable platform 25 and a plurality of second telescopic elements 26 disposed between the first movable platform 22 and the second movable platform 25, a side of the second movable platform 25 relatively far away from the static platform 21 is fixedly connected to the executing assembly 30, and both ends of each second telescopic element 26 are rotationally connected to the first movable platform 22 and the second movable platform 25 respectively.

With this disposition, the second movable platform 25 can perform displacement activities based on the first movable platform 22, thereby increasing the activity range of the surgical instrument 32 so as to assist doctors to realize more complex surgical contents.

In the present embodiment, the telecentric manipulating assembly 20 forms two interconnected parallel platforms, that is, a first level parallel platform and a second level parallel platform respectively, in this case, the first level parallel platform includes the static platform 21, the first movable platform 22 and the first telescopic element 23 located between the static platform 21 and the first movable platform 22 above, the second level parallel platform includes the second movable platform 25 and the second telescopic element 26 located between the first movable platform 22 and the second movable platform 25.

It should be additionally noted that each level parallel platform may include two platforms and telescopic elements between the two platforms. For example, the first level parallel platform includes two platforms, that is, the first movable platform 22 and the static platform 21 respectively; the second level parallel platform may also include two platforms, that is, the second movable platform 25 and an installation platform fixed on the first movable platform (not shown in the figure).

Of course, except for the two platforms required for the first level parallel platform, the corresponding installation platform may also be omitted for the second level parallel platform and a larger level parallel platform, while one of the previous level parallel platforms acts as the installation platform. For example, the second level parallel platform includes two platforms which are the second movable platform 25 and the first movable platform 22 in the first level parallel platform respectively, that is, in this case, the first movable platform 22 is shared by the two level parallel platforms.

To sum up, the feature "each level parallel platform includes two opposite platforms and telescopic elements between the two platforms" described herein has two cases, one is that each level parallel platform has two platforms, and the two platforms are not shared among different level parallel platforms; and one is that each level parallel platform implement its own relative movement between the two platforms by sharing the adjacent level platforms.

Specifically, the rotation driving part 27 is installed on a side of the second movable platform 25 close to the executing assembly 30, and the rotation driving part 27 is directly connected to the executing rod 31 and can drive the executing rod 31 to rotate synchronously with the surgical instrument 32. The first deflection driving part 281, the second deflection driving part 282 and the open-close driving part 283 are all installed at a side of the second movable platform 25 far away from the executing assembly 30, and are located in the middle of the second movable platform 25, which will not affect the arrangement of the second telescopic elements 26.

In order to reduce the motion error and facilitate realizing kinematic analysis at the same time, in one embodiment of the present disclosure, the arrangement manner of the respective rotation connecting points 24 between a plurality of the second telescopic elements 26 and the first movable platform 22 on the first movable platform 22 is the same as the arrangement manner of the respective rotation connecting points 24 between a plurality of the first telescopic elements 23 and the static platform 21 on the static platform 21; and/or, the arrangement manner of the respective rotation connecting points 24 between a plurality of the second telescopic elements 26 and the second movable platform 25 on the second movable platform 25 is the same as the arrangement manner of the respective rotation connecting points 24 between a plurality of the first telescopic elements 23 and the first movable platform 22 on the first movable platform 22.

With this disposition, not only the kinematic analysis steps between the first movable platform 22 and the second movable platform 25 may be simplified, but also the motion error of the second movable platform 25 may be reduced; moreover, it is easy to process, and the processing accuracy may be ensured.

It may be understood that in other embodiments, the respective rotation connecting points 24 may also be arranged in other ways, as long as the flexible movements of the first movable platform 22 and the second movable platform 25 can be realized.

In order to further reduce the motion error and further simplify the kinematic analysis steps at the same time, in one embodiment of the present disclosure, when respective axial directions of the first movable platform 22, the second movable platform 25 and the static platform 21 are in a coincide d state, each first telescopic element 23 and the corresponding second telescopic element 26 are disposed in parallel with each other.

With this disposition, the kinematic analysis steps between the first movable platform 22 and the second movable platform 25 may be further simplified, and the motion error of the second movable platform 25 is reduced.

It may be understood that in other embodiments, each first telescopic element 23 and the corresponding second telescopic element 26 may also be arranged in other ways, as long as the flexible movements of the first movable platform 22 and the second movable platform 25 can be realized.

In order to realize the large-scale positioning of the executing assembly 30, in one embodiment of the present disclosure, the presurgical positioning assembly 10 includes a moving arm 11 and a telescopic arm 12, and the telescopic arm 12 is disposed between the moving arm 11 and the static platform 21 and is rotationally connected to the moving arm 11.

With this disposition, the executing assembly 30 can realize a large-scale position adjustment under the driving of the presurgical positioning assembly 10, so as to realize the two-stage adjustment of the executing assembly 30 by using the telecentric manipulating assembly 20 and the presurgical positioning assembly 10, which is conducive to the high efficiency and refinement of position adjustment.

In one embodiment thereof, the telescopic arm 12 is telescoped by disposing a telescopic electric cylinder, and the moving arm 11 is moved and rotated by disposing a rotating joint. The telescopic electric cylinder has one degree of freedom, the rotating joint has at least one degree of freedom, and collaborative use of the two may enable the presurgical positioning assembly 10 to have at least two degrees of freedom, so as to realize a large-scale movement and quickly reach the vicinity of the patient's lesion.

The surgical robotic arm applicable to the surgical robot needs to drive the surgical instrument to perform the surgical operation, and the surgical instrument needs to realizing reaching the patient's body by extending into a tiny wound opened on the skin surface. This requires the surgical instrument to perform the surgical operation in a stable and non-trembling state with the tiny wound opened on the skin surface as a fixed point. However, the current surgical robotic arm suitable for the surgical robot cannot fully meet the use requirements in clinical manifestations, especially the lack of mechanical detection of the surgical operation performed by the surgical instrument, the doctors cannot obtain the mechanical feedback of the pathological tissue to the surgical instrument under the surgical operation, and the lack of mechanical information reduces the accuracy in the surgical operation by the doctors.

The surgical robotic arm 100 provided by the present disclosure avoids the winding of the steel strip in the surgical robotic arm by disposing the overall synchronously rotated executing assembly 30, and can realize the accurate measurement of mechanical information on the surgical instrument 32.

Specifically, the surgical robotic arm 100 also includes a sensor 29 (for example, as shown in FIG. 1), and the sensor is connected to the executing rod 31 and is used to detect at least one of the environmental force or the environmental torque received by the surgical instrument 32.

It should be additionally noted that the interconnection between the sensor and the executing rod 31 may be a direct contact therebetween, that is, the executing rod 31 directly contacts a measuring surface of the sensor; and may also be an indirect contact between the sensor and the executing rod 31, that is, the executing rod 31 is connected to an intermediate transition element, and the intermediate transition element then directly contacts the measuring surface of the sensor, so that the executing rod 31 is connected to the sensor.

It should also be explained that at least one of the environmental force or the environmental torque received by the surgical instrument 32 referred to herein are at least one of the force or the torque exerted by the external environment on the surgical instrument 32, such as the reaction force provided by the tissue when it is clamped by the surgical instrument 32; when a plurality of forces are coupled to the surgical instrument 32 and a torque action is formed, the surgical instrument 32 will be affected by both the environmental force and the environmental torque.

In the present embodiment, the sensor is a six-axis force and torque sensor. In this case, the sensor may synchronously sense at least one of the environmental force or the environmental torque received by the surgical instrument 32 located on its own measurement surface. It may be understood that when only the environmental force on the surgical instrument 32 needs to be measured, the sensor can be selected as a force sensor; and when only the environmental torque on the surgical instrument 32 needs to be measured, the sensor can be selected as a torque sensor.

Due to the synchronous rotation of the executing rod 31 and the surgical instrument 32, the connecting cables (not shown in the figure) inside the executing rod 31 move in an integral way, thereby avoiding the disadvantage that the reliable mechanical sensor cannot be realized due to the winding of the connecting cables in the traditional structure, so that the sensor may realize the accurate measurement of at least one of the environmental force or the environmental torque received by the surgical instrument 32.

The sensor in the present embodiment is installed on the first movable platform 22 or in a device relatively located at a front end of the first movable platform 22 in the surgical robotic arm 100.

It should be noted that the sensor is installed in the device relatively located at the front end of the first movable platform 22 in the surgical robotic arm 100, which means that the installation position of the sensor is located at a side of the first movable platform 22 relatively far away from the presurgical positioning assembly 10, that is, the sensor can be installed on a rod body of the executing rod 31 or directly on the surgical instrument 32.

In this case, the sensor, relative to the surgical instrument 32, may not be disturbed by the winding when the first telescopic element 23 is telescoped, and the accuracy during the measurement has been greatly improved.

The rotation driving part 27 is installed on the first movable platform 22, and the sensor 29 is installed on the rotation driving part 27 (as shown in FIG. 1). In this case, the rotation driving part 27 can drive the sensor, the executing rod 31 and the surgical instrument 32 to all rotate synchronously relative to the first movable platform 22 along an axial direction of the executing rod 31.

The rotation driving part 27 and the sensor are installed on the first movable platform 22, which may provide great convenience for the installation of the rotation driving part 27 and the sensor, and compared with the solution that the sensor is installed in a device relatively located at the front end of the first movable platform 22 in the surgical robotic arm 100, the installation accuracy is greatly reduced.

The surgical robotic arm 100 provided by the present disclosure forms a parallel mechanism through the first movable platform 22, the static platform 21, and the plurality of first telescopic elements 23 located between the first movable platform 22 and the static platform 21, and a motion accuracy of the executing assembly 30 at the end is improved by using an error non-cumulative characteristic of the parallel mechanism; furthermore, a mutually independent driving manner among the plurality of first telescopic elements 23 improves the load capacity, and a surgical operation of the executing assembly 30 under a larger load may be guaranteed. Furthermore, compared with the serial mechanism, the parallel mechanism has the characteristics of high accuracy, high stiffness and large load. For the same load and accuracy requirements, the mechanical manufacturing process requirements are relatively low, and this may greatly reduce the manufacturing cost of the surgical robotic arm 100; the structural characteristics of the surgical robotic arm 100 enable the rotation and other movements of the surgical instrument to be driven without the use of steel cables, the phenomenon such as distortion of the steel cables may not occur, so as to greatly improve the service life of the surgical instrument and reduce its use cost; furthermore, it is also easy to realize the accurate detection of forces.

The present disclosure further provides a surgical robot, including a surgical robotic arm 100, and the surgical robotic arm 100 is a surgical robotic arm 100 of any one of the above.

The surgical robot provided by the present disclosure improves its own motion accuracy and load capacity by applying the above surgical robotic arm 100, may realize clinical surgeries with higher accuracy and greater strength, and has a wider application prospect.

According to various embodiments of the present disclosure, a surgical robotic arm is provided, including a presurgical positioning assembly, a telecentric manipulating assembly and an executing assembly, the telecentric manipulating assembly includes a static platform, a first movable platform and a plurality of first telescopic elements disposed between the static platform and the first movable platform, a side of the static platform relatively far away from the first movable platform is fixedly connected to the presurgical positioning assembly, a side of the first movable platform relatively far away from the static platform is fixedly connected to the executing assembly, and both ends of each first telescopic element are rotationally connected to the static platform and the first movable platform respectively;

the executing assembly has a preset telecentric fixed point; coordinated extension and retraction of the plurality of first telescopic elements can control the first movable platform to move relative to the static platform and drive the executing assembly to extend and retract and swing; a swing center of the executing assembly is the telecentric fixed point; and a telescopic path of the executing assembly passes through the telecentric fixed point.

According to the surgical robotic arm provided by an embodiment of the present disclosure, a parallel mechanism is formed by the first movable platform, the static platform, and the plurality of first telescopic elements located between the first movable platform and the static platform, and a motion accuracy of the executing assembly at the end is improved by using an error non-cumulative characteristic of the parallel mechanism; furthermore, a mutually independent driving manner among the plurality of first telescopic elements improves the load capacity, and a surgical operation of the executing assembly under a larger load may be guaranteed.

In order to improve the flexibility of the surgical robotic arm, in one embodiment of the present disclosure, a swing limit angle of the executing assembly relative to the telecentric fixed point is disposed as ±20°, and the executing assembly can swing in a conical space with a telescopic path of the executing assembly as an axis and a vertex angle of 40°.

With this disposition, the executing assembly is relatively flexible, can move in a relatively large range, and can assist doctors to realize more complex surgical operations.

In order to improve the stability of the surgical robotic arm, a plurality of rotation connecting points between each of the first telescopic elements and the first movable platform are disposed in a common circle, and rotation connecting points between each of the first telescopic elements and the static platform are disposed in a common circle; and a circular diameter enclosed and formed by the rotation connecting points on the static platform is 1 to 2 times the circular diameter enclosed and formed by the rotation connecting points on the first movable platform.

With this disposition, the first movable platform has fewer tremors in the process of moving relative to the static platform, and a total error between the respective first telescopic elements may compensate for each other, so as to improve the stability of the surgical robotic arm.

In order to further improve the stability of the surgical robotic arm, the circular diameter enclosed and formed by the rotation connecting points on the static platform is 1.7 times the circular diameter enclosed and formed by the rotation connecting points on the first movable platform.

With this disposition, the first movable platform has a minimum tremor in the process of moving relative to the static platform, furthermore, a space volume occupied by the first movable platform and the static platform may be relatively compressed, and there is the most balanced combination between structure lightweight and high performance.

In order to realize the rotating connection between the first telescopic element and the first movable platform and the static platform, both ends of the first telescopic element are respectively provided with a ball hinge joint and a Hooke hinge joint; the first telescopic element is connected to one of the static platform and the first movable platform through the ball hinge joint, and is connected to the other of the static platform and the first movable platform through the Hooke hinge joint.

With this disposition, both ends of the first telescopic element can be rotationally connected with the first movable platform and the static platform, respectively, and the connection performance of the first telescopic element is better.

In order to take into account the cost on the basis of realizing the rotating connection between the first telescopic element and the first movable platform and the static platform, the surgical robotic arm further includes a cylinder sleeve, and the cylinder sleeve is sleeved and rotationally connected to the first telescopic element; Hooke hinge joints are respectively disposed on one end of the cylinder sleeve relatively far away from the first telescopic element and on one end of the first telescopic element relatively far away from the cylinder sleeve; one of the cylinder sleeve and the first telescopic element is connected to the first movable platform through the corresponding Hooke hinge joint; and the other of the cylinder sleeve and the first telescopic element is connected to the static platform through the corresponding Hooke hinge joint.

With this disposition, the first telescopic element may realize the power transmission between the first movable platform and the static platform through the Hooke hinge joint with low manufacturing difficulty and low cost, and it is not necessary to dispose an expensive and easily damaged ball hinge joint, thereby having a better cost performance advantage.

In order to improve the moving stability of the surgical robotic arm, the number of the first telescopic elements is six, and the respective rotation connecting points between the first telescopic element and the first movable platform are all disposed spaced apart from each other; and the respective rotation connecting points between the first telescopic element and the static platform are all disposed spaced apart from each other.

With this disposition, by adopting the distribution form of interval rotation connecting points, the tremor interference between the respective first telescopic elements is reduced, and the moving stability of the surgical robotic arm can be further improved.

In order to improve the moving stability of the surgical robotic arm, the respective rotation connecting points between the first telescopic element and the first movable platform are paired in a nearby way, a first included angle is correspondingly formed between each group of the same pair of two rotation connecting points and a center of the first movable platform, and a size of each of the first included angles is equal.

With this disposition, the rotation connecting points of the first telescopic element on the first movable platform will be disposed in pairs, thus, the moving stability of the surgical robotic arm is improved, and kinematic analysis is realized easily at the same time.

In order to further improve the moving stability of the surgical robotic arm, an angle range of the first included angle $\alpha$ is 15° to 60°.

With this disposition, the included angle range between the respective rotation connecting points is in a better section, which is not only conducive to ensuring the moving stability, but also can facilitate realizing the moving analysis of telescopic amount of each first telescopic element through a relatively appropriate included angle range.

In order to further improve the moving stability of the surgical robotic arm, the respective rotation connecting points between the first telescopic element and the static platform are paired in a nearby way, a second included angle is correspondingly formed between each group of the same pair of two rotation connecting points and a center of the static platform, and a size of each of the second included angles is equal.

With this disposition, the rotation connecting points of the first telescopic element on the static platform will be disposed in pairs, thus, the moving stability of the surgical robotic arm is improved, and kinematic analysis is realized easily at the same time.

In order to further improve the moving stability of the surgical robotic arm, an angle range of the second included angle is 60° to 105°.

With this disposition, the included angle range between the respective rotation connecting points is in a better section, which is not only conducive to ensuring the moving stability, but also can facilitate realizing the moving analysis of telescopic amount of each first telescopic element through a relatively appropriate included angle range.

With this disposition, the included angle range between the respective rotation connecting points is in a better section, which is not only conducive to ensuring the moving stability, but also can facilitate realizing the moving analysis of telescopic amount of each first telescopic element through a relatively appropriate included angle range.

In order to avoid the occurrence of winding of transmission cables during the rotation of the surgical instrument, the executing assembly includes an executing rod and a surgical instrument disposed at one end of the executing rod relatively far away from the first movable platform, the first movable platform is provided with a rotation driving part, the rotation driving part is connected to the executing rod and can drive the executing rod and the surgical instrument to rotate synchronously along an axial direction of the executing rod.

With this disposition, the surgical instrument will rotate synchronously with the executing rod, so as to avoid the mutual winding of the transmission cables when rotating relative to the executing rod.

In order to make the movement of the surgical instrument more flexible and accurate, the first movable platform is also provided with a first deflection driving part, a second deflection driving part and an open-close driving part, the executing rod is hollow and contains transmission cables, and the surgical instrument is connected to the first deflection driving part, the second deflection driving part and the open-close driving part through the transmission cable; and the first deflection driving part and the second deflection driving part can respectively drive the surgical instrument to deflect in two different staggered directions through the transmission cable, and the open-close driving part can drive the surgical instrument to open and close through the transmission cable.

With this disposition, the surgical instrument can be flexibly deflected and opened and closed under the cooperative action of the first deflection driving part, the second deflection driving part and the open-close driving part, and the simultaneous driving of a plurality of driving parts may reduce the displacement error and delay error during driving.

In order to realize more complex surgical contents, the telecentric manipulating assembly includes multi-level parallel platforms interconnected, and each level the parallel platform includes two opposite platforms and telescopic elements between the two platforms;

and in the multi-level parallel platforms, the parallel platform relatively close to the presurgical positioning assembly is a first level parallel platform, and the first level parallel platform includes the static platform, the first movable platform and a plurality of first telescopic elements disposed between the static platform and the first movable platform.

With this disposition, the multi-level parallel platform can superimpose and expand the activity range of the surgical instrument to assist the doctor to realize more complex surgical contents.

In order to take into account the complexity of the surgical contents and the accuracy of the control, the number of the parallel platform is two, the telecentric manipulating assembly also includes a second level parallel platform connected to the first level parallel platform, the second level parallel platform includes a second movable platform and a plurality of second telescopic elements disposed between the first movable platform and the second movable platform, a side of the second movable platform relatively far away from the static platform is fixedly connected to the executing assembly, and both ends of each of the second telescopic elements are rotationally connected to the first movable platform and the second movable platform respectively.

With this disposition, the second movable platform can perform displacement activities taking the first movable platform as a basis, the structure design of a two-level parallel platform takes into account both the satisfaction of surgical complexity and the guarantee of control accuracy, thereby avoiding the excessive superposition of control errors caused by excessive levels.

In order to reduce the motion error and facilitate realizing kinematic analysis at the same time, the arrangement manner of the respective rotation connecting points between the plurality of second telescopic elements and the first movable platform on the first movable platform is the same as the arrangement manner of the respective rotation connecting points between the plurality of first telescopic elements and the static platform on the static platform; and/or the arrangement manner of the respective rotation connecting points between the plurality of second telescopic elements and the second movable platform on the second movable platform is the same as the arrangement manner of the respective rotation connecting points between the plurality of first telescopic elements and the first movable platform on the first movable platform.

With this disposition, not only the kinematic analysis steps between the first movable platform and the second movable platform may be simplified, but also the motion error of the second movable platform may be reduced; moreover, it is easy to process, and the processing accuracy may be ensured.

In order to further reduce the motion error and further simplify the kinematic analysis steps at the same time, when respective axial directions of the first movable platform, the second movable platform and the static platform are in a coincided state, the first telescopic element and the corresponding second telescopic element are disposed in parallel with each other.

With this disposition, the kinematic analysis steps between the first movable platform and the second movable platform may be further simplified, and the motion error of the second movable platform is reduced.

In order to realize large-scale positioning of the executing assembly, the presurgical positioning assembly includes a moving arm and a telescopic arm, and the telescopic arm is disposed between the moving arm and the static platform and is rotationally connected to the moving arm.

With this disposition, the executing assembly may realize a large-scale position adjustment under the driving of the presurgical positioning assembly, so as to realize the two-stage adjustment of the executing assembly by using the telecentric manipulating assembly and the positioning assembly, which is conducive to the high efficiency and refinement of position adjustment.

In order to realize the detection of mechanical information, the first movable platform is also provided with a sensor; the sensor is connected to the executing rod and used to detect at least one of the environmental force or the environmental torque received by the surgical instrument.

With this disposition, the surgical robotic arm may make connecting cables inside the executing rod move as an integral since the executing rod and the surgical instrument are disposed to rotate synchronously, thereby avoiding the disadvantage that the reliable mechanical sensor cannot be realized due to the winding of the connecting cables in the traditional structure, so that the sensor may realize the accurate measurement of at least one of the environmental force or the environmental torque received by the surgical instrument.

In order to improve the detection accuracy, the sensor is installed on the first movable platform or in a device relatively located at a front end of the first movable platform in the surgical robotic arm.

With this disposition, the sensor, relative to the surgical instrument, may not be disturbed by the winding when the first telescopic element is telescoped, and the accuracy during the measurement has been greatly improved.

In order to further improve the detection accuracy, the sensor is installed on the rotation driving part, and the rotation driving part can drive the sensor, the executing rod and the surgical instrument to all rotate synchronously along the axial direction of the executing rod.

With this disposition, the rotation driving part and the sensor are installed on the first movable platform, which may provide great convenience for the installation of the rotation driving part and the sensor, and compared with the solution that the sensor is installed in a device relatively located at the front end of the first movable platform in the surgical robotic arm, the installation accuracy is greatly reduced.

An embodiment of the present disclosure further provides a surgical robot, including a surgical robotic arm, and the surgical robotic arm is the surgical robotic arm according to various embodiments of the present disclosure.

The surgical robot provided by an embodiment of the present disclosure improves its own motion accuracy and load capacity by applying the above surgical robotic arm, can realize clinical surgeries with higher accuracy and greater strength, and has a wider application prospect.

In the depiction of the present disclosure, it should be understood that the orientation or position relationships indicated by the orientation words such as "front, back, upper, lower, left, right", "horizontal, vertical, vertical, horizontal" and "top and bottom" are usually based on the orientation or position relationships shown in the drawings, which are only for the convenience of describing the present disclosure and simplifying the depiction. In the case without contrary explanations, these orientation words do not indicate or imply that the device or element referred to must have a specific orientation or be constructed and operated in a specific orientation, thus, they cannot be understood as limits of the protection scope of the present disclosure; the orientation words "inside and outside" refer to the inside and outside of the contour relative to each component itself.

For the convenience of depiction, spatial relative terms, such as "above", "on", "on the upper surface", "upper" and so on, can be used here to describe the spatial relationship between one device or feature and other devices or features as shown in the figure. It should be understood that the spatial relative terms are intended to include different orientations in use or operation in addition to the orientations of devices described in the figure. For example, if the devices in the drawings are inverted, the devices described as "above other devices or configurations" or "on other devices or configurations" will be positioned as "below other devices or configurations" or "under other devices or configurations" afterwards. Therefore, the exemplary term "above" may include both "above" and "below" orientations. The device may also be positioned in other different ways (rotated by 90 degrees or in other orientations), and the spatial relative depiction used here is explained accordingly.

The respective technical features of the above embodiments can be combined arbitrarily. In order to simplify the depiction, all possible combinations of the respective technical features in the above embodiments are not described. However, as long as there is no contradiction in the combination of these technical features, they all should be considered as scopes recorded by the description.

Those ordinary technical persons in the technical field should recognize that the above embodiments are only used to explain the present disclosure, rather than being used to limit the present disclosure, and the appropriate modifications and changes made to the above embodiments are all within the scope claimed by the present disclosure only if they are within the substantive spirit range of the present disclosure.

The invention claimed is:

1. A surgical robotic arm, comprising a presurgical positioning assembly, a telecentric manipulating assembly and an executing assembly, wherein the telecentric manipulating assembly comprises a static platform, a first movable platform and a plurality of first telescopic elements disposed parallelly between the static platform and the first movable platform, a parallel mechanism is formed by the static platform, the first movable platform and the plurality of first telescopic elements, a side of the static platform opposite to the first movable platform is connected to the presurgical positioning assembly, a side of the first movable platform opposite to the static platform is connected to the executing assembly, and both ends of each first telescopic element are rotationally connected to the static platform and the first movable platform respectively, and the executing assembly has a preset telecentric fixed point, coordinated extension and retraction of the plurality of first telescopic elements is capable of controlling the first movable platform to move relative to the static platform and drive the executing assembly to extend and retract and swing, a swing center of the executing assembly is the preset telecentric fixed point, and a telescopic path of the executing assembly passes through the preset telecentric fixed point, wherein the preset telecentric fixed point is a fixed point selected and fixed along a length direction of the executing assembly, and a position of the preset telecentric fixed point is selected in a single surgical operation and is changed in different surgical operations.

2. The surgical robotic arm of claim 1, wherein a swing limit angle of the executing assembly relative to the preset telecentric fixed point is disposed as ±20°, and the executing assembly is capable of swinging in a conical space with the telescopic path of the executing assembly as an axis and a vertex angle of 40°.

3. The surgical robotic arm of claim 1, wherein a plurality of first rotation connecting points between each of the plurality of first telescopic elements and the first movable platform are disposed in a circle, and second rotation connecting points between each of the plurality of first telescopic elements and the static platform are disposed in a circle; and a circular diameter enclosed and formed by the second rotation connecting points is 1 to 2 times the circular diameter enclosed and formed by the first rotation connecting points.

4. The surgical robotic arm of claim 3, wherein the circular diameter enclosed and formed by the second rotation connecting points is 1.7 times the circular diameter enclosed and formed by the first rotation connecting points.

5. The surgical robotic arm of claim 1, wherein both ends of the each first telescopic element are respectively provided with a ball hinge joint and a Hooke hinge joint; the each first telescopic element is connected to one of the static platform and the first movable platform through the ball hinge joint, and is connected to the other of the static platform and the first movable platform through the Hooke hinge joint.

6. The surgical robotic arm of claim 1, wherein the number of the plurality of first telescopic elements is six, and first rotation connecting points between the each first telescopic element and the first movable platform are all disposed spaced apart from each other; and second rotation connecting points between the each first telescopic element and the static platform are all disposed spaced apart from each other.

7. The surgical robotic arm of claim 6, wherein the first rotation connecting points between the each first telescopic element and the first movable platform are paired, a first included angle is correspondingly formed between each group of the pair of first rotation connecting points and a center of the first movable platform, and a size of each of the first included angles is equal.

8. The surgical robotic arm of claim 7, wherein an angle range of the first included angle is 15° to 60°.

9. The surgical robotic arm of claim 8, wherein the second rotation connecting points between the each first telescopic element and the static platform are paired, a second included angle is correspondingly formed between each group of a pair of second rotation connecting points and a center of the static platform, and a size of each of the second included angles is equal.

10. The surgical robotic arm of claim 9, wherein an angle range of the second included angle is 60° to 105°.

11. The surgical robotic arm of claim 1, wherein the executing assembly comprises an executing rod and a surgical instrument disposed at one end of the executing rod opposite to the first movable platform, the first movable platform is provided with a rotation driving part, the rotation driving part is connected to the executing rod and is capable of driving the executing rod and the surgical instrument to rotate synchronously along an axial direction of the executing rod.

12. The surgical robotic arm of claim 11, wherein the first movable platform is further provided with a first deflection driving part, a second deflection driving part and an open-close driving part, the executing rod is hollow and contains transmission cable, and the surgical instrument is connected to the first deflection driving part, the second deflection driving part and the open-close driving part through the transmission cable; and the first deflection driving part and the second deflection driving part are capable of respectively driving the surgical instrument to deflect in two different staggered directions through the transmission cable, and the open-close driving part is capable of driving the surgical instrument to open and close through the transmission cable.

13. The surgical robotic arm of claim 11, wherein the first movable platform is further provided with a sensor; and the sensor is connected to the executing rod and used to detect an environmental force and/or environmental torque received by the surgical instrument.

14. The surgical robotic arm of claim 13, wherein the sensor is installed on the first movable platform or in a device located at a front end of the first movable platform in the surgical robotic arm.

15. The surgical robotic arm of claim 14, wherein the sensor is installed on the rotation driving part, and the rotation driving part is capable of driving the sensor, the executing rod and the surgical instrument to all rotate synchronously along the axial direction of the executing rod.

16. The surgical robot of claim 15, wherein the first movable platform is further provided with a sensor; and the sensor is connected to the executing rod and used to detect an environmental force and/or environmental torque received by the surgical instrument.

17. The surgical robot of claim 13, wherein a swing limit angle of the executing assembly relative to the preset telecentric fixed point is disposed as ±20°, and the executing assembly is capable of swinging in a conical space with the telescopic path of the executing assembly as an axis and a vertex angle of 40°.

18. The surgical robot of claim 17, wherein the sensor is installed on the first movable platform or in a device located at a front end of the first movable platform in the surgical robotic arm.

19. The surgical robot of claim 13, wherein the executing assembly comprises an executing rod and a surgical instrument disposed at one end of the executing rod opposite to the first movable platform, the first movable platform is provided with a rotation driving part, the rotation driving part is connected to the executing rod and is capable of driving the executing rod and the surgical instrument to rotate synchronously along an axial direction of the executing rod.

20. The surgical robot of claim 19, wherein the sensor is installed on the rotation driving part, and the rotation driving part is capable of driving the sensor, the executing rod and the surgical instrument to all rotate synchronously along the axial direction of the executing rod.

21. The surgical robot of claim 13, wherein the telecentric manipulating assembly comprises multi-level parallel platforms interconnected, and at each level, the parallel platform comprises two opposite platforms and respective telescopic elements between the two opposite platforms;

wherein the multi-level parallel platforms comprise a first level parallel platform closest to the presurgical positioning assembly, and the first level parallel platform comprises the static platform, the first movable platform and the plurality of first telescopic elements disposed between the static platform and the first movable platform.

22. The surgical robotic arm of claim 1, wherein the telecentric manipulating assembly comprises multi-level parallel platforms interconnected, and at each level, the parallel platform comprises two opposite platforms and respective telescopic elements between the two opposite platforms;

wherein the multi-level parallel platforms comprise a first level parallel platform closest to the presurgical positioning assembly, and the first level parallel platform comprises the static platform, the first movable platform and the plurality of first telescopic elements disposed between the static platform and the first movable platform.

23. The surgical robotic arm of claim 22, wherein the multi-level parallel platforms further comprise a second level parallel platform connected to the first level parallel platform, the second level parallel platform comprises a second movable platform and a plurality of second telescopic elements disposed between the first movable platform and the second movable platform, a side of the second movable platform opposite to the static platform is fixedly connected to the executing assembly, and both ends of each of the second telescopic elements are rotationally connected to the first movable platform and the second movable platform respectively.

24. The surgical robotic arm of claim 23, wherein when respective axial directions of the first movable platform, the second movable platform and the static platform are in a coincided state, each of the first telescopic elements and each of the corresponding second telescopic elements are disposed in parallel with each other.

25. A surgical robot, comprising a surgical robotic arm, wherein the surgical robotic arm comprises a presurgical positioning assembly, a telecentric manipulating assembly and an executing assembly, wherein the telecentric manipulating assembly comprises a static platform, a first movable platform and a plurality of first telescopic elements disposed parallelly between the static platform and the first movable platform, a parallel mechanism is formed by the static platform, the first movable platform, and the plurality of first telescopic elements, a side of the static platform opposite to the first movable platform is connected to the presurgical positioning assembly, a side of the first movable platform opposite to the static platform is connected to the executing assembly, and both ends of each first telescopic element are rotationally connected to the static platform and the first movable platform respectively, and the executing assembly has a preset telecentric fixed point, coordinated extension and retraction of the plurality of first telescopic elements is capable of controlling the first movable platform to move relative to the static platform and drive the executing assembly to extend and retract and swing, a swing center of the executing assembly is preset telecentric fixed point, and a telescopic path of the executing assembly passes through the preset telecentric fixed point, wherein the preset telecentric fixed point is a fixed point selected and fixed along a length direction of the executing assembly, and a position of the preset telecentric fixed point is selected in a single surgical operation and is changed in different surgical operations.

\* \* \* \* \*